(12) United States Patent
Flower

(10) Patent No.: US 8,361,775 B2
(45) Date of Patent: Jan. 29, 2013

(54) IMAGING METHODS AND COMPOSITIONS COMPRISING FLUORESCENT DYES ASSOCIATED WITH VIRAL COMPONENTS FOR NERVE IMAGING

(75) Inventor: Robert W. Flower, Hunt Valley, MD (US)

(73) Assignee: Novadaq Technologies Inc., Mississauga, Ontario (CA)

( * ) Notice: Subject to any disclaimer, the term of this patent is extended or adjusted under 35 U.S.C. 154(b) by 128 days.

(21) Appl. No.: 12/466,122

(22) Filed: May 14, 2009

(65) Prior Publication Data

US 2009/0285762 A1 Nov. 19, 2009

Related U.S. Application Data

(60) Provisional application No. 61/127,659, filed on May 14, 2008, provisional application No. 61/082,981, filed on Jul. 23, 2008.

(51) Int. Cl.
*C12N 7/00* (2006.01)
*A61K 49/00* (2006.01)
*A61K 35/76* (2006.01)

(52) U.S. Cl. ............... 435/235.1; 424/9.6; 424/93.6

(58) Field of Classification Search .................. None
See application file for complete search history.

(56) References Cited

U.S. PATENT DOCUMENTS 6,399,354 B1 6/2002 Knipe et al.

FOREIGN PATENT DOCUMENTS

| WO | WO02061390 A2 | 8/2002 |
| WO | WO 03/006658 * | 1/2003 |
| WO | WO2007028032 A2 | 3/2007 |

OTHER PUBLICATIONS

Schellingerhout et al, Gene Therapy 7:1648-1655, 2000.*
Vaccine definition, Stedman's Medical Dictionary 28th edition. Downladed from the internet <<http://www.pdrel.com/View/StedmanSearch/DocumentRetrive.aspx?documentId=42862>> on May 21, 2011.*
Prophylaxis definition, Stedman's Medical Dictionary 28th edition. Downladed from the internet <<http://www.pdrel.com/View/StedmanSearch/DocumentRetrive.aspx?documentId=33301>> on May 21, 2011.*
Fields Virology, 5$^{th}$ edition, 2007, chapter 67. Downloaded from the internet <<http://ovidsp.tx.ovid.com/sp-3.4.1b/ovidweb.cgi>> on May 27, 2011.*
Peng et al. Virology 216:184-196, 1996.*
Smith et al (PNAS 97: 9264-9269, 2000).*
Enquist et al (Veterinary Microbiology 86:5-16, 2002).*
McKee et al (Cancer Research 66:2509-2513, 2006).*
Schellingerhout et al (Gene Therapy 7:1648-1655, 2000).*
Gitis et al (Water Research 36:4227-4234, 2003).*
Van Strijp et al (Archives of Virology 104:287-298, 1989).*
Feierbach et al (Journal of Virology 81:6846-6857, Jul. 2007) teaches nerve imaging in vitro using replication-defective pseudorabies virus expressing GFP.*
Cohen (Journal of Infectious Disease 197(Supple 2): S237-241, Mar. 1, 2008).*
Mahalingham et al (Journal of Neurovirology 4:438-444, 1998).*
Glossary, Nature, downloaded from the internet <<http://www.nature.com/nrg/journal/v4/n10/glossary/nrg1183_glossary.html>> on May 27, 2011.*
Fields' Virology / editors-, David M. Knipe et al.—5th ed. 2007. Lippincott Williams & Wilkins, Philadelphia, PA. pp. 2780-2781.*
Pyner S. et al., "Tracing functionally identified neurones in a multisynaptic pathway in the hamster and rat using herpes simplex virus expressing gree fluorescent protein", Experimental Physiology 2001 GB, vol. 86, No. 6, pp. 695-702.
Sugimoto K. et al., "Simultaneous tracking of capsid, tegument, and envelope protein localization in living cells infected with triply fluorescent herpes simplex virus 1" Journal of Virology US, vol. 82, No. 11, Mar. 2008, pp. 5198-5211.
Smith G. A. et al., "Herpesviruses use bidirectional fast-axonal transport to spread in sensory neurons", Proceedings of the National Academy of Sciences of the United States of America Mar. 13, 2001 US, vol. 98, No. 6, pp. 3466-3470.
Ekstrand M. I. et al., "The alpha-herpesviruses: molecular pathfinders in nervous system circuits", Trends in Molecular Medicine, Elsevier Current Trends, vol. 14, No. 3, Feb. 14, 2008, pp. 134-140.
International Search Report and Written Opinion of corresponding application PCT/US2009/043975 dated Jul. 29, 2009.

* cited by examiner

*Primary Examiner* — Mary E Mosher
(74) *Attorney, Agent, or Firm* — Rissman Hendricks & Oliverio LLP

(57) ABSTRACT

Disclosed herein are compositions and methods for imaging nerve cells. The composition comprises a fluorescent dye; and a viral component selected from a neurotropic, replication-defective virus, a viral protein of a neurotropic virus, and a capsid of a neurotropic virus. Although the fluorescent dye in itself cannot penetrate nerve cells, the fluorescent dye is bound to the viral component to form a dye/viral component complex that is capable of penetrating nerve cells.

3 Claims, 11 Drawing Sheets

FIG. 4D                                  FIG. 4E

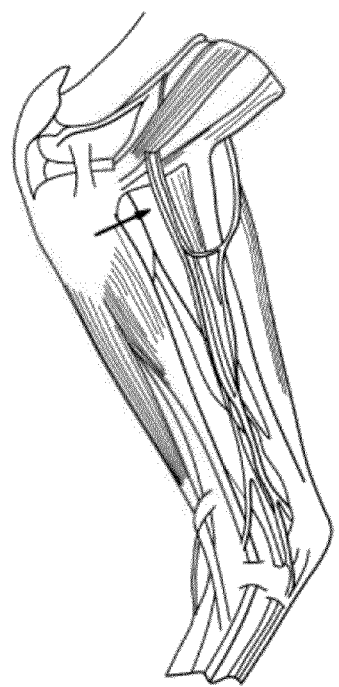
FIG. 5C
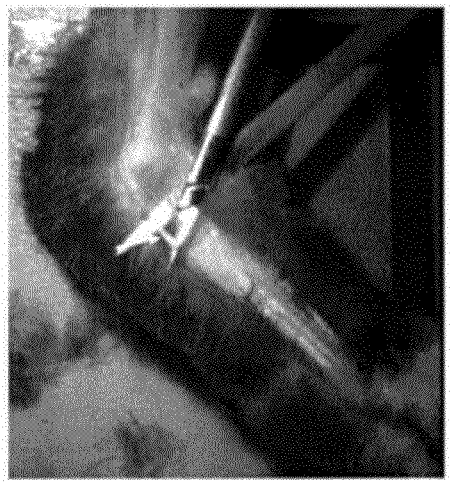 
FIG. 5D  FIG. 5E

IMAGING METHODS AND COMPOSITIONS COMPRISING FLUORESCENT DYES ASSOCIATED WITH VIRAL COMPONENTS FOR NERVE IMAGING

RELATED APPLICATION

This application claims the benefit of priority under 35 U.S.C. §119(e) to U.S. Prov. App. No. 61/127,659, filed May 14, 2008, and U.S. Prov. App. No. 61/082,981, filed Jul. 23, 2008, the disclosures of which are incorporated herein by reference.

FIELD OF THE INVENTION

Disclosed herein are compositions and methods relating to the field of medical imaging.

BACKGROUND OF THE INVENTION

Iatrogenic nerve injury can result in debilitating loss of function in humans. Common causes of iatrogenic nerve injury include surgical failure, traction or pressure lesions, hematoma, or inadequate positioning of the patient (Fercan Komurcu, MD et al., 2005, Annals of Plastic Surgery, 54(2): 135-139).

For example, nerves are often imaged during prostatectomy procedures. By way of background, prostate cancer is the most common type of cancer in American men. One common treatment option is removal of cancerous prostate tissue (i.e., prostatectomy) before the cancer spreads locally and before metastasis. Radical prostatectomy complications include incontinence and impotence. A significant percentage of men undergoing radical prostatectomy procedures become impotent due to injury to the cavernous nerves during the surgery.

The risk of iatrogenic nerve injury may be reduced by avoiding injury to the bundles of nerves that run along the surface of the prostate gland and are needed for an erection. Successful nerve sparing surgery, however, is often difficult to achieve because of the difficulty in distinguishing between the prostate tissue and the innervating nerve tissue.

There exists a need for improved imaging methods and compositions for nerve imaging.

SUMMARY OF THE INVENTION

Disclosed herein are compositions and methods for imaging nerves. The nerves can be located in different areas of a subject.

Also disclosed herein is the discovery that binding a fluorescent dye to a viral component (e.g., virus, viral proteins, capsids) capable of penetrating nerve axons can form a dye/viral component complex that can penetrate nerve axons, thus allowing improved nerve cell imaging. One embodiment provides a composition comprising:
 a fluorescent dye; and
 a viral component selected from a neurotropic, replication-defective virus, a viral protein of a neurotropic virus, and a capsid of a neurotropic virus,
 wherein the fluorescent dye is bound to the viral component to form a dye/viral component complex that is capable of penetrating nerve cells.

In this and other embodiments disclosed herein, neurotropic, replication-defective viruses can be, for example, attenuated or inactivated viral components that are capable of penetrating nerve cells. In another embodiment, the composition can be a vaccine comprising the fluorescent dye and a viral component selected from a neurotropic virus, a viral protein of a neurotropic virus, and a capsid of a neurotropic virus. Accordingly, another embodiment provides a vaccine, comprising:
 a fluorescent dye; and
 a viral component selected from a neurotropic virus, a viral protein of a neurotropic virus, and a capsid of a neurotropic virus,
 wherein the fluorescent dye is bound to the viral component to form a dye/viral component complex that is capable of penetrating nerve cells.

Another embodiment provides a method of making a composition, comprising:
 combining a fluorescent dye with a viral component selected from a neurotropic, replication-defective virus, a viral protein of a neurotropic virus, and a capsid of a neurotropic virus,
 allowing the fluorescent dye to be bound to the viral component to form a dye/viral component complex that is capable of penetrating nerve cells.

Another embodiment provides methods for imaging nerves and/or diagnosing nerve abnormalities and/or conditions. The methods include the steps of (a) administering a composition, as disclosed herein, to the subject, (b) allowing the dye/viral component complex to penetrate nerve cells, (c) applying a sufficient amount of radiant energy to the subject such that the dye fluoresces, (d) intra-operatively obtaining a fluorescence image of the subject. The method can include the step of observing the fluorescence image to view one or more nerves in the subject, or observing the fluorescence image to determine whether one or more nerves is transected.

Accordingly, another embodiment provides a method for reducing the risk of iatrogenic injury to a subject during a surgical procedure, comprising:
 (a) administering a composition to the subject, the composition comprising:
  a fluorescent dye; and
  a viral component selected from a neurotropic, replication-defective virus, a viral protein of a neurotropic virus, and a capsid of a neurotropic virus,
  wherein the fluorescent dye is bound to the viral component to form a dye/viral component complex;
 (b) allowing the dye/viral component complex to penetrate nerve cells;
 (c) applying a sufficient amount of radiant energy to the subject such that the dye fluoresces;
 (d) intraoperatively obtaining a fluorescence image of the subject; and
 (e) observing the fluorescence image to view one or more nerves in the subject.

Another embodiment provides a method for diagnosing a nerve condition, comprising:
 (a) administering a composition to the subject, the composition comprising:
  a fluorescent dye; and
  a viral component selected from a neurotropic, replication-defective virus, a viral protein of a neurotropic virus, and a capsid of a neurotropic virus,
  wherein the fluorescent dye is bound to the viral component to form a dye/viral component complex;
 (b) allowing the dye/viral component complex to penetrate nerve cells;
 (c) applying a sufficient amount of radiant energy to the subject such that the dye fluoresces;
 (d) intraoperatively obtaining a fluorescence image of the subject; and (e) observing the fluorescence image to determine whether the nerve is transected.

Other embodiments provide a kit containing the compositions disclosed herein along with instructions to use the composition according to one or more of the methods described herein. In other embodiments, the kit includes one or more ingredients, reagents, dyes, viruses, precursors, or other tools that can be used to make the compositions disclosed herein, along with instructions to use the composition according to one or more of the methods described herein.

BRIEF DESCRIPTION OF THE DRAWINGS

FIG. 4D are fluorescence images of (i) the dissected fluorescent dorsal root ganglion from the left side of the spine of the mouse of Example 4 in white light only, with a short segment of its axons on the right side of the ganglion, and (ii) the corresponding ganglion from the right side of the spine, whose right footpad axons were not injected;

FIG. 4E are fluorescence images of (i) the ganglion of FIG. 4D(i) and (ii) the ganglion of FIG. 4D(ii);

FIG. 5C shows an anatomical drawing of a rabbit right limb for comparison with the fluorescence image;

FIG. 5D is an image of an isolated segment of the saphenous nerve, in visible white light;

FIG. 5E is a fluorescence image showing an isolated segment of the saphenous nerve with ICG/HSV-2ΔRR complex fluorescence;

DETAILED DESCRIPTION

Figure 1:
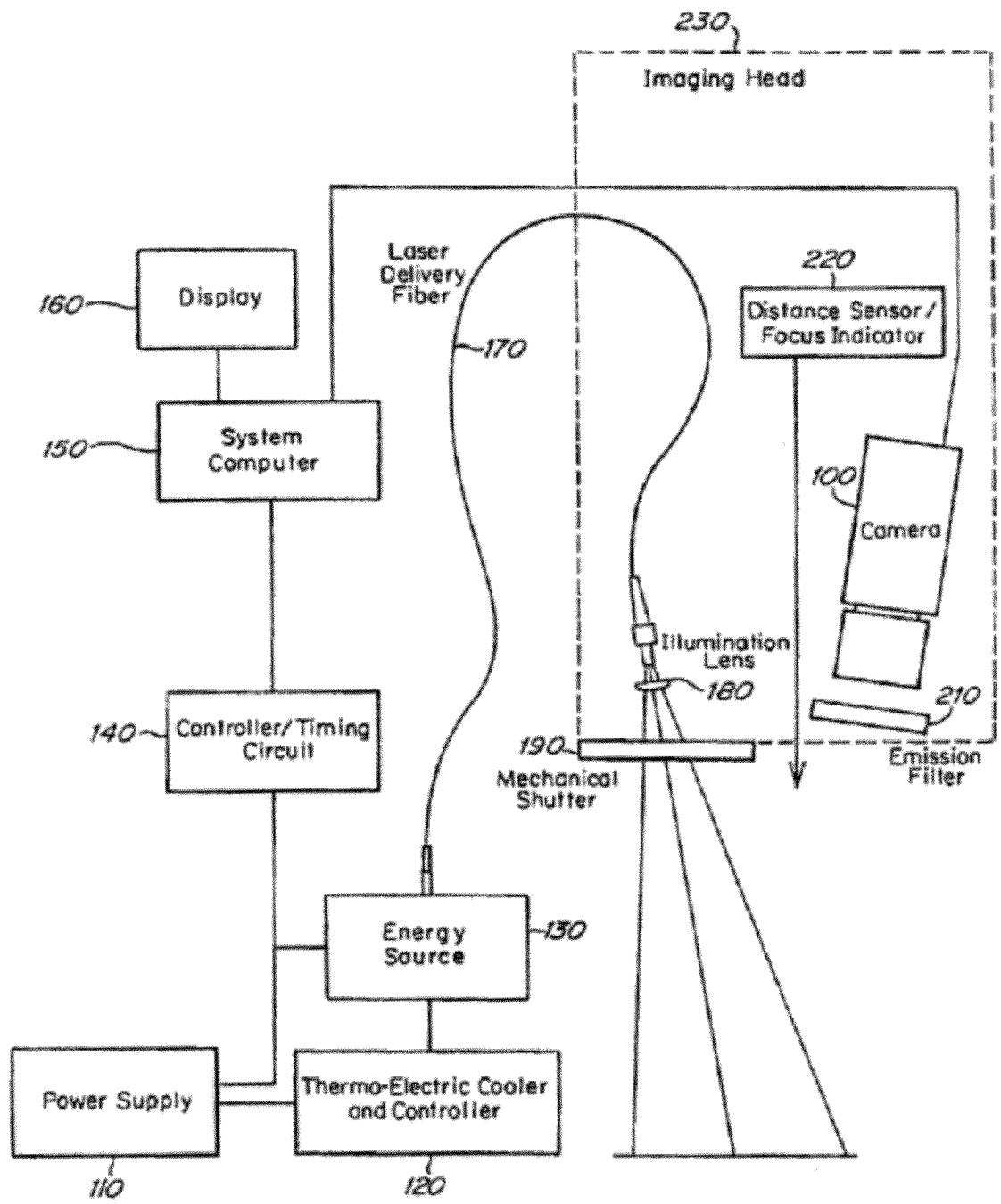
FIG. 1 schematically depicts a system for medical imaging.

One embodiment provides compositions for nerve imaging.

In one embodiment, the composition includes a dye, such as a fluorescent dye used for medical imaging. Many dyes, however, are not suitable for imaging certain portions of the body, such as nerves, as the dyes are typically incapable of penetrating nerve cells. Disclosed herein is the discovery that a neurotropic viral component, i.e., a viral component capable of penetrating nerve cells, can be used to axonally transport a dye through parts or all of a network of nerves. This can be achieved by forming a complex of a dye bound to the viral component.

Dyes

As used herein, the term "fluorescent dye" or "dye" means a small molecule or a protein or other polymer or macromolecule that fluoresces by emitting light in the visible or near-infrared wavelength range upon excitation by radiant light energy of an appropriate wavelength.

Suitable fluorescent dyes include any non-toxic dye that fluoresces when exposed to radiant energy, e.g. light. In certain embodiments the dye is a fluorescent dye that emits light in the near-infrared spectrum. In some embodiments, the dye may not be lipid soluble, while in other embodiments, it may be lipid soluble. In certain embodiments the dye is a tricarbocyanine dye such as indocyanine green (ICG), is sold by Akorn, Inc. (Buffalo Grove, Ill.). ICG dye is FDA approved for human use. In other embodiments, the dye is infracyanine green. In other embodiments the dye is selected from fluorescein isothiocyanate, rhodamine, phycoerythrin, phycocyanin, allophycocyanin, o-phthaldehyde, fluorescamine, Rose Bengal, trypan blue, fluoro-gold, 3-indocyanine-green-acyl-1,3-thiazolidine-thione, green fluorescent protein, red fluorescent protein, yellow fluorescent protein, blue fluorescent protein and other fluorescent proteins. The dyes may be mixed or combined. In some embodiments, dye analogs may be used. A "dye analog" is a dye that has been chemically modified, but still retains its ability to fluoresce when exposed to radiant energy of an appropriate wavelength.

In one embodiment the dye is a fluorescent protein such as green fluorescent protein covalently bound to a protein in a viral capsid, constructed by replacing the viral protein gene with the same viral protein gene but fused to the green fluorescent protein gene. In one embodiment green fluorescent protein is covalently bound to a neutropic virus protein that penetrates nerve cells.

Viral Components

In one embodiment, the viral component is selected from a virus, viral proteins, and capsids. In one embodiment, the viral protein is the capsid or capsid protein. In one embodiment, the viral protein is a viral protein analog. In one embodiment the viral proteins and analogs are capable of penetrating a nerve cell on their own, without being part of a viral capsid or whole virus. In another embodiment the viral proteins and analogs may be part of a viral capsid or whole virus that itself penetrates a nerve cell. Analogs have a different nucleic acid structure resulting in conservative amino acid changes, which although they alter the primary sequence of the protein or peptide, do not normally alter its function.

Conservative amino acid substitutions typically include substitutions within the following groups:
- glycine, alanine;
- valine, isoleucine, leucine;
- aspartic acid, glutamic acid;
- asparagine, glutamine;
- serine, threonine;
- lysine, arginine;
- phenylalanine, tyrosine.

In one embodiment, the viral protein and analogs thereof may be isolated before the dye is bound to them.

Because it is used in medical applications, this component is nonvirulent or "replication-defective." As used herein, the term "replication-defective" means failing to form virus particles (virus progeny) in the target cell (a nerve cell). In one embodiment, "replication-defective" refers to the inability to reproduce. A "replication-defective" virus can also refer to an attenuated virus. In one embodiment, attenuated viruses are live viruses that are of low virulence. In one embodiment, attenuated viruses do not replicate. In another embodiment, they may express viral antigens in infected cells without replication. In another embodiment, the attenuated viruses slowly replicate and produce attenuated virus progeny.

In one embodiment, the viral component is not neurovirulent.

In one embodiment, a virus is rendered replication-defective via mutation or inactivation by heat, light (e.g., UV light), or chemical treatment. The dosage and wavelengths of ultraviolet ("UV") light required to kill certain viruses are well known. For example, http://www.americanairandwater.com/uv-facts/uv-dosage.htm lists the dosage of UV light that will inhibit colony formation of certain viruses, reproduced in Table 1 below:

TABLE 1

| Virus | Energy Dosage of Ultraviolet radiation (UV dose) in μWs/cm² needed for kill factor | |
| --- | --- | --- |
| | 90% (1 log reduction) | 99% (1 log reduction) |
| Bacteriophage - E. Coli | 2,600 | 6,600 |
| Infectious Hepatitis | 5,800 | 8,000 |
| Influenza | 3,400 | 6,600 |
| Poliovirus - Poliomyelitis | 3,150 | 6,600 |
| Tobacco mosaic | 240,000 | 440,000 |

In one embodiment, the mutation can be accomplished by removing or inactivating viral genetic material (such as RNA for RNA viruses, or DNA for DNA viruses) or proteins required for viral replication, cytopathic effects, or cell lysis. In one embodiment, the virus is a mutant of rabies virus, for example, Imovax (Sanofi Pasteur SA).

In another embodiment a replication defective virus is a vaccine. "Vaccine" as used herein refers to a non-virulent composition (comprising one or more viral components) that improves immunity towards a disease. In another embodiment a vaccine may be used as the virus component, such as the Zostavax® vaccine (Merck & Co., Inc., Whitehouse Station, N.J.). Accordingly, another embodiment provides a vaccine, comprising:
- a fluorescent dye; and
- a viral component selected from a neurotropic virus, a viral protein of a neurotropic virus, and a capsid of a neurotropic virus,
- wherein the fluorescent dye is bound to the viral component to form a dye/viral component complex that is capable of penetrating nerve cells.

The viral component is neurotropic in that it penetrates cells of the nervous system (e.g., motor nerves and/or sensory nerves). In some embodiments, the virus is one that is transported axonally through the nervous system. It should be safe to use in humans. Thus, in certain embodiments, any viral component that is capable of penetrating a nerve cell, and binding with dye may be used so long as it is not lytic and preferably so long that it does not cause cytopathic effect.

The neurotropic property of the viral component is exploited for imaging by allowing the fluorescent dye to be bound to the component, thereby forming a dye/viral component complex that too is neurotropic, i.e., capable of penetrating cells of the nervous system. Binding between the dye and the virus or viral proteins may occur through van der Waal interactions, dipole-dipole interactions, cation-pi interaction interactions, hydrogen bonding, ionic bonding, covalent bonding, or any other type of binding sufficient for the dye to enter nerve cells with virus or viral particles. In some embodiments, the dye and the virus or viral proteins may bind directly, meaning that they are not bonded or associated by an intermediary, interposed linker between the dye and its associated virus or viral particles.

In one embodiment the capsid of a neurotropic virus, with bound fluorescent dye, may be used.

In some embodiments, the virus is herpes virus, and may be Herpes Simplex Virus Type 2 (HSV-2) or a mutant thereof. HSV-2 infects cells of the nervous system. The HSV-2 gene ICP10 encodes a ribonucleotide reductase (RR) enzyme comprised of two subunits, referred to as the large and small subunits, encoded by the UL39 and UL40 genes, respectively. The HSV-2 ICP10 gene (GeneBank No. M12700) is described in U.S. Pat. Nos. 6,013,265, 6,054,131, and 6,207,168.

In one example of an HSV-2 mutant, the ribonucleotide reductase (RR) domain is deleted from ICP10. Elimination of this domain is useful in that the resulting mutant is rendered replication-defective.

In one embodiment, the virus is the mutant form of HSV-2, designated ICP10ΔRR, in which the ribonucleotide reductase domain of ICP10 is replaced with the gene encoding LacZ. The ICP10ΔRR virus is known in the art (Peng et al., 1996, Virology, 216:184-196; LacZ-specific staining facilitates detection of cells that are infected with the mutant virus). ICP10ΔRR can also have a deletion of the RR gene, without the addition of the LacZ gene. One could replace the LacZ gene with any gene of interest. Any HSV-2 mutant in which the RR domain is deleted or inactivated may be useful. The HSV-2 ICP10ΔRR mutant will be referred to as HSV-2 ΔRR herein.

In another embodiment, the virus may be herpes varicellae (herpes zoster virus).

Standard molecular biology procedures known in the art may be used to make suitable viruses. Exemplary procedures are disclosed in Sambrook et al. (1989, Molecular Cloning: A Laboratory Manual, Cold Spring Harbor Laboratory, New York), in Ausubel et al. (1997, Current Protocols in Molecular Biology, John Wiley & Sons, New York), and in Gerhardt et al. (eds., 1994, Methods for General and Molecular Bacteriology, American Society for Microbiology, Washington, D.C.).

Compositions

As described above, in some embodiments, the composition includes a dye bound to a replication-defective viral component. In certain embodiments, the composition includes a dye bound to a viral protein or inactivated virus, as further described herein. Compositions may be administered to a subject for nerve imaging.

Accordingly, another embodiment provides a method of making a composition, comprising:

combining a fluorescent dye with a viral component selected from a neurotropic, replication-defective virus, a viral protein of a neurotropic virus, and a capsid of a neurotropic virus, allowing the fluorescent dye to be bound to the viral component to form a dye/viral component complex that is capable of penetrating nerve cells.

In some embodiments, the composition comprises little or no dye that is not bound to the virus, or viral protein. For example, the amount of dye used to make the composition may be titrated to the amount of virus or viral protein used. Similarly, extraneous (unbound) dye may be removed from the composition through dialyses or use of a sucrose gradient.

Also disclosed herein is the preparation and use of compositions described herein. Such a composition may consist of the active ingredient alone, in a form suitable for administration to a subject, or the composition may comprise the active ingredient and one or more pharmaceutically acceptable carriers, one or more additional ingredients, or some combination of these. The active ingredient may be present in the composition in the form of a physiologically acceptable ester or salt, such as in combination with a physiologically acceptable cation or anion, as is well known in the art.

As used herein, the term "active ingredient" means a viral component such as a neurotropic virus, viral capsid or viral protein to which a fluorescent dye is bound.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient, which is compatible with any other ingredients of the composition and which is not deleterious to the subject to whom the composition be administered.

The formulations of the compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desirable single- or multi-dose unit.

Although the descriptions of compositions provided herein are principally directed to compositions that are suitable for human administration, it will be understood by the skilled artisan that such compositions are generally suitable for administration to animals of all sorts. Modification of compositions suitable for human administration in order to render the compositions suitable for administration to various animals is well understood, and the ordinarily skilled veterinary pharmacologist can design and perform such modification with merely ordinary, if any, experimentation. Subjects to whom administration of the compositions is contemplated include, but are not limited to, human and non-human primates, and other mammals.

The compositions may be prepared, packaged, or sold in formulations suitable for parenteral, intravenous, ophthalmic, intrathecal or any other route of administration.

The compositions may be prepared, packaged, or sold in bulk, as a single unit dose, or as a plurality of single unit doses. As used herein, a "unit dose" is any discrete amount of the composition comprising a predetermined amount of the active ingredient. The amount of the active ingredient is generally equal to the dosage of the active ingredient that would be administered to a subject or a convenient fraction of such a dosage such as, for example, one-half or one-third of such a dosage.

As used herein, "parenteral administration" of a composition includes any route of administration characterized by physical breaching of a tissue of a subject and administration of the composition through the breach in the tissue. Parenteral administration thus includes, but is not limited to, administration of a composition by injection, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry form (i.e. powder, granular, or lyophilized) for reconstitution with a suitable vehicle (e.g. sterile pyrogen-free water) prior to parenteral administration of the reconstituted composition.

Doses that may be administered to an animal, e.g., a human, range from about $10^2$ to about $10^8$, or from about $10^2$ to about $10^4$ or from about $10^3$ to about $10^8$ plaque forming units of virus per gram of body weight. In another embodiment, the dose ranges from, for example, about $10^{-4}$ mg to about $2\times10^{-3}$ mg of dye/g of body weight). For example, the animal experiments described in the experimental section below were performed with ICG dye and the following amount of virus: (a) $4.2\times10^4$ pfu of virus per gram of body weight for mice, and (b) 972.8 pfu per gram body weight for the rabbit.

Methods of Imaging

One embodiment provides a method for imaging at least one nerve of a subject. The image may be obtained intraoperatively. Thus the area where surgery is to be performed or nearby regions may be surgically exposed. The method comprises: (a) administering the composition described herein to form a dye/viral component complex, (b) allowing the dye/viral component complex to penetrate nerve cells; (c) applying a sufficient amount of radiant energy to the area such that the dye fluoresces, (d) intra-operatively obtaining a fluorescence image, and (e) observing the fluorescence image to determine the presence or absence of at least one nerve in the fluorescence image.

In one embodiment, "observing the fluorescence image" can refer to reviewing a still image (whether printed or on screen), or real-time on a video monitor, in addition to other methods of observing images. In one embodiment, the individual images of nerves (i.e., nerve maps) made possible by binding a fluorescent dye to a virus component (e.g., a viral vector) can be used for diagnostic purposes and for documentation of nerve location. In one embodiment, one use for nerve mapping is intraoperative. It is envisioned that this technology can be used for dye-tagging nerves for use in fluoroscopy, an imaging technique commonly used by physicians to obtain real-time moving images of the internal structures of a patient. For example, intraoperative visualization of the surgical field of view, by whatever conventional means are available, can occur such that location and/or recognition of nerves—especially small branches thereof—is inadequate to assure nerve-sparing surgery. In such situations, intraoperative fluoroscopic use of the present technological innovation will be critical to successful outcomes.

Based on the experiments reported below, it was estimated that dye fluorescence might move at the rate of about 2 cm/hr, or faster, in a retrograde fashion through nerves. This fast speed of dye flow may allow the compositions to be administered just hours (or longer) before imaging is performed. The composition, including the dye, can be administered a sufficient time before imaging such that the dye travels to the area to be imaged and is present in such area at the time of imaging. The amount of time required may depend on the nerve imaging application and the administration site. As an example, the composition may be administered up to or less than 1, 2, 3, 4, 5, 6, 7, or 8 hours before imaging in certain procedures, for example, based on the distance that the dye needs to travel to the imaging site. In one embodiment, the composition is administered no more than 1, 2 or 3 hours before imaging.

By observing the fluorescence image the surgical team can determine the absence or presence of a nerve in the image. Often nerves may be identified by their size, shape, and gross location using conventional surgical field illumination with visible light. Frequently, however, the contrast between the nerves—especially small branches thereof—and the underlying tissues is so poor that without the significant contrast afforded by causing the nerves to fluoresce, they cannot be observed at all. The surgical team may further determine the location of one or more specific nerve(s) by observing the fluorescence image. The surgical team can thus use information about the presence/absence or location of one or more nerves to determine how they will perform the surgical procedure. For example, based on information obtained through use of the methods, the surgical team may decide to make an incision at a point on the subject where they are less likely to inadvertently cut or surgically contact a particular nerve based on the perceived absence of a nerve from that area.

Other embodiments contemplate obtaining a plurality of images. The plurality of images may be compared to each other to determine that a nerve has not been damaged, e.g., inadvertently cut.

The information obtained from the obtained image can aid in grafting the ends of the nerves if they are transected. In the event of transection, nerve grafts can be applied directly to the ends to facilitate sprouting of regenerative neural fibers. In this case, the light visible from the fluorescence of the ends of transected nerves provides a target to guide the anastomosis of the nerves by the nerve graft.

Methods of Diagnosis

Another embodiment provides a method of diagnosing a nerve condition, e.g., whether a nerve has been injured or transected, or successfully resected, such as during a surgical procedure. In one embodiment, the method of diagnosis includes the steps of (a) administering the composition disclosed herein to the subject, (b) allowing the dye/viral component complex to penetrate nerve cells; (c) applying a sufficient amount of radiant energy to the subject such that the dye fluoresces, (d) intraoperatively obtaining a fluorescence image of the subject, and (e) observing the fluorescence image to either view one or more nerves in the subject and/or determine whether one or more nerves is transected.

Thus, by viewing an image of a nerve, the user can determine whether a particular nerve has been transected. In some embodiments, the image is used to determine whether a transected nerve has been corrected (i.e., resected).

Images obtained by these methods can be used to help guide neural grafting when unintended transactions occur or when they cannot otherwise be avoided. In some embodiments, an image will be observed after the neural graft is performed to confirm that the nerve has been successfully resected.

The skilled practitioner will be able to determine whether a particular nerve is transected by viewing the images obtained according to the disclosed methods. For example, jagged lines may indicate transection. Similarly, if a nerve appears longer or wider in a first image than in a later image, this may also indicate that the nerve has been transected. Conversely, if a nerve appears longer or wider in a later image than in an earlier image, this may indicate that it has been resected. Thus, in some embodiments, the method contemplates obtaining multiple images.

Devices for Imaging

Once administered, the fluorescent dye in the composition is excited to fluorescence, and its emitted light is captured by a camera. A suitable device is the SPY system (Novadaq Technologies Inc., Mississauga, Canada), or as described in U.S. Pat. No. 6,915,154.

Generally, a suitable device has a light source capable of exciting the fluorescent dye and a camera capable of capturing the emitted dye fluorescence.

FIG. 1 illustrates an example of a system suitable for exciting and imaging the fluorescent dye. In certain embodiments, power supply 110 provides energy to thermoelectric cooler and controller 120, light energy source 130 and controller/timing circuit 140. The controller 120 controls the temperature of the light energy source 130. For example, the temperature of a diode laser affects its operating wavelength, (e.g., a 0.3 nm shift per degree Celsius). In some embodiments, as described herein, the light energy source 130 may not be a diode laser, and hence a controller 120 may not be necessary. Controller/timing circuit 140 times the light energy source 130 to the detector/camera 100 through computer 150. It also includes image-processing software on computer 150 readable medium. Computer 150 is in electrical communication with camera 100 and display 160. Display 160 receives image data from computer 150 and displays it. As described above, in some embodiments, the light energy source 130 is a laser. It has a fiber 170 through which light energy is transmitted. Fiber 170 conducts light to illumination lens 180 through which light passes toward a target field of view when mechanical shutter 190 is open. A barrier filter 210 may be used to filter light emanating from the field of view in the wavelengths range above or below that at which the fluorescent dye is excited. In other embodiments, the light energy source 130 may be an LED. It would directly illuminate the tissue of interest in the field of view (i.e., no fiber 170 may be required.) Camera 100 captures radiation emitted by the dye after it is excited and transmits detected image data to computer 150. The lens 180, fiber 170, and camera 100 are part of imaging head 230. The head 230 may be an articulating head. In some embodiments, head 230 further includes a distance sensor/focus indicator 220. The components of the systems are further described herein.

In certain embodiments, radiant energy is applied to the tissue of interest, in an amount sufficient to cause a fluorescent dye to fluoresce thereby permitting the tissue of interest to be imaged. In some embodiments the source of the light energy is a laser. The laser may be comprised of a driver and diode. Preferably, the laser is a high power laser diode (HPLDs). Examples of HPLDs include AlInGaAsP lasers and GaAs lasers which are well known in the art. Such sources can be single diodes (single emitters), or diode-laser bars, which are made from edge emitting semiconductor chips. The laser may optionally include a filter, e.g. a band-pass filter, to ensure that the emitted radiation is of a substantially uniform wavelength. The laser may comprise optics for diverging the laser beam. The optics may be adjustable permitting variation in the field of illumination. The adjustable optics may also be used to provide even illumination over a given area (e.g., field of view).

In some embodiments the source output is continuous or quasi continuous. In other embodiments the laser output is pulsed. The pulsed output may be synchronized with image acquisition by using a pulse generator. In some embodiments the laser pulse may last for at least 3 femtoseconds. In some embodiments the laser output lasts for about 30 seconds. In other embodiments the laser output lasts about 0.5 seconds-about 60 seconds. A suitable repetition rate for the pulsed laser may be in the range of any of the following:, about 1 Hz-about 80 MHz, about 10 Hz-about 100 Hz, about 100 Hz-about 1 kHz, about 1 kHz-about 100 kHz, about 100 kHz-about 80 MHz. In some embodiments the laser may be operated at power output of about 1.8, about 2.2, or about 2.5 watts. In other embodiments the laser may be operated at power output in the range of about 1-about 4 watts. In still other embodiments the average power is less than 5 watts.

In some embodiments the source of the energy is an incandescent light with an appropriate filter so as to provide a suitable wavelength of light to induce the fluorescent dye to fluoresce. In yet other embodiments the light source is a light emitting diode (LED).

In some embodiments the radiant energy may have a wavelength in the range of 150 nm-1500 nm. The energy may be comprised of infrared light. In some embodiments the excitation light has a wavelength of about 805 nm. In certain embodiments the excitation light has a wavelength in the range of about 805 nm-850 nm. In one embodiment, the excitation light energy is administered at a wavelength that is shorter than the emitted wavelength, i.e., detection wavelength. The excitation light energy may be administered diffusely so as not to damage the irradiated tissue. In some embodiments the excitation light is administered over an area of about 7.5 cm×7.5 cm. In other embodiments the light is administered over an area in the range of about 1 cm×1 cm to about 20 cm×20 cm. In one embodiment, the area is about 25 to 100 $cm^2$. As described above, multiple dyes may be used in some embodiments. In these embodiments, multiple light sources may be used, e.g., a first laser to excite a first dye and a second laser to excite the second dye. The skilled artisan will understand that the light source will be chosen or configured to excite a particular dye. In other embodiments, a single light source may be configured to excite multiple dyes, e.g., by alternating the wavelength at which energy is emitted.

The imaging head 230 may be comprised of a light sensor, e.g., a camera 100. Image acquisition may be achieved using any sensor capable of detecting a fluorescent signal. Examples include silicon-based sensors, composite metal oxide semi oxide (CMOS) sensors and photographic film. In one embodiment the sensor comprises a camera, e.g. charge coupled device (CCD). Examples of a CCD include the Hitachi KP-M2; KP-M3 (Hitachi, Tokyo, Japan).

The camera may be comprised of a means for focusing the image. Certain embodiments encompass a manual means for focusing an image. Other embodiments encompass an automated means for focusing an image. The camera may further be comprised of a lens system that permits magnification of an image field.

In some embodiments, the relative positioning of the camera and laser is fixed so as to enhance clarity and minimize background noise. In these embodiments, the laser is located at an angle of less than about 85° with respect to the axes of the laser and the camera. In other embodiments, the laser is located at an angle from about 20° to about 70° with respect to the axes of the laser and the camera. In some embodiments, the laser is located at an angle greater than about 85° with respect to the axes of the laser and the camera. Such an angle may be, for example, 90°.

In certain embodiments the camera relays the captured image to an analog to digital converter and then through image capture and processing software running on a computer. The image may be stored in any suitable medium, e.g., a hard drive, an optical disk, magnetic tape. The camera may also direct images to a television/VCR system such that the images may be displayed in real time, recorded and played back at a later time. Thus, imaging can be performed in real time or with delay.

In certain embodiments the computer 150 is a personal computer comprising at least 512 Megabytes of random access memory (RAM) and at least 10 Gigabytes of storage. In some embodiments the computer 150 may contain a Pentium IV processor (Intel, Santa Clara, Calif.). In some embodiments the computer 150 may also have a CD and DVD drive. The drive may have read and write functionality. The system also provides image-processing software.

In certain embodiments an endoscope may be used to excite a fluorescent dye in a composition and to detect its fluorescence, e.g., for interventional applications. It includes a sensor and a source of radiant energy. The endoscope may be comprised of optical fibers. In certain other embodiments a microscope comprising a sensor and radiation source may be used, e.g., a surgical microscope. In some embodiments the sensor comprises a video camera. In certain embodiments the sensor may capture images at the rate of at least 10 per second, at least 15 per second, at least 20 per second, at least 30 per second, or at least 50 per second. Thus, certain embodiments contemplate a plurality of images. In other embodiments the invention contemplates one image.

Figure 2:
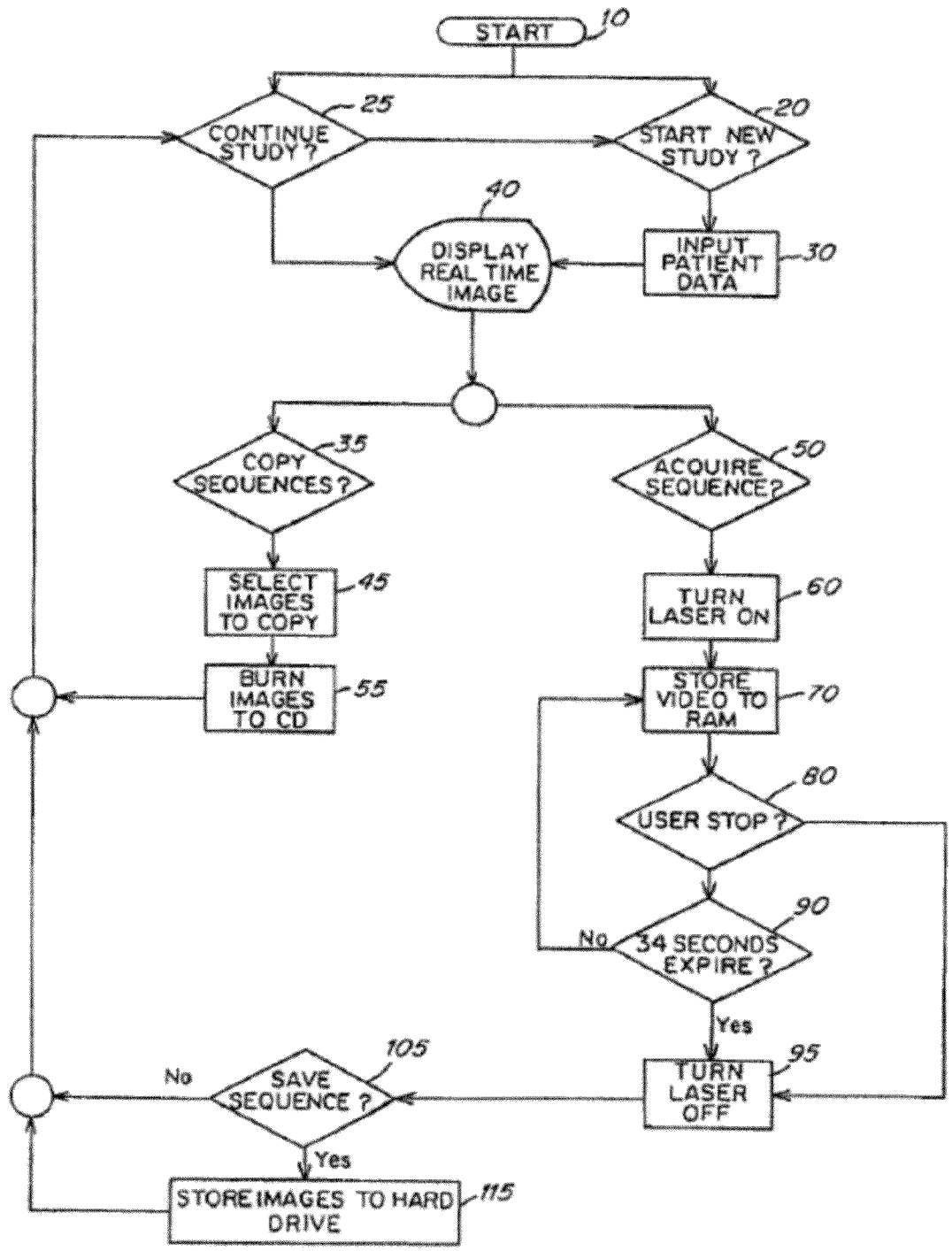
FIG. 2 is a flowchart depicting algorithms for medical imaging that can be performed by software installed on a computer processor.

FIG. 2 illustrates one embodiment of an imaging method. This method may be carried out by programmed instructions stored on computer readable media, hardware or firmware. (The skilled artisan will understand that such software includes instructions stored on computer-readable medium.) When executed, the software program provides instructions to the computer processor as described below. The skilled artisan will further understand that the computer is in communication with the laser, sensor and display as described herein.

At start (step 10) the user may be presented with multiple dialog boxes or other common user interface paradigms. For example, the user may be queried about whether he wishes to start a new study (step 20). If the user indicates that he does, he may be instructed to input or otherwise select a patient for the study. For example, the user may be prompted to choose a name from a list linked to a database that is accessible to the computer. Alternately, he may be prompted to input a patient identifier. The computer may then access the database to determine the existence of additional information associated with the patient, and preferably to obtain such information. In a preferred embodiment, the software requires the user to input or otherwise select values for Patient First Name, Last Name and ID number fields. Most preferably, sufficient information is inputted or otherwise loaded so that images may be stored according to the Digital Imaging and Communications in Medicine (DICOM) standard. The DICOM Standard is a product of the DICOM Standards Committee and its many international working groups. Day-to-day operations are managed by the National Electrical Manufacturers Association (Rosslyn, Va.). The standard is publicly available at the website http://medical.nema.org/, and is incorporated herein by reference in its entirety.

After patient data are input, the monitor or other display displays images captured by the camera or other sensor in communication with the computer (step 40). At this point, the user can change the position, orientation, gain or other parameter of the camera to obtain a desired view of the patient.

Alternately, the user may choose to continue a study (step 25) at start 10. Upon such indication, the process proceeds to step 40.

Once the image is displayed, the user is prompted to indicate whether he wishes to copy sequences (step 35) or acquire sequence (step 50). The term "sequences" refers to data associated with real-time images captured by a camera or other sensor in communication with the computer. Once the user indicates that he wants to acquire images from the sensor in step 50, the computer causes the laser to turn on, and it stores the video sequence obtained from the sensor in RAM (step 70). Real-time images continue to be displayed on the display. The user is then queried about whether he wishes to turn the laser off (step 80). If he indicates that he does, the computer causes the laser to shut off (step 100). Alternately, if the user does not indicate that he wants to shut off the laser, the computer determines whether a pre-determined amount of time (e.g., 34 seconds) has elapsed from step 60. Once that pre-determined amount of time has elapsed, the computer causes the laser to shut off. The video sequences continue to be stored in RAM until the laser is turned off. Once the laser is turned off, the user is queried as to whether he wishes to save the sequence (step 105). If he indicates in the affirmative, then the sequences are stored to hard drive (step 115) or other media.

Returning now to step 40 for purposes of describing the software, once the real-time image is displayed, the user is queried as to whether he wishes to copy sequences (step 35). If the user indicates that he does, the images associated with the study are selected and burned on compact disk or other selected media (step 55). Alternatively, the software may allow the user to select specific images for storage on selected media. Preferably, the image(s) are stored in a format that is compatible with a picture archiving and computer system, for example in a DICOM format.

In another embodiment, the camera may also direct images to a LCD monitor or other display (e.g., television/VCR system, etc.) such that the image(s) may be displayed in real time and/or recorded and played back at a later time. Since the image(s) may be used to guide all or part of the surgical procedure, the image(s) may be displayed throughout the length of the surgical procedure. In other embodiments, the image(s) may be displayed for less than the entire length of the surgical procedure. In another embodiment the software permits manipulating the images after acquisition, such as zooming, region of interest selection, change of brightness and contrast, and displaying multiple images simultaneously.

In some embodiments the system comprises a sterile drape. The sterile drape covers the articulating arm to prevent or minimize the risk of contamination of the subject. The sterile drape may have an aperture in it. The aperture may be covered with a material that is capable of transmitting radiant energy, e.g., infrared light generated by a laser.

Definitions

The articles "a" and "an" are used herein to refer to one or to more than one (i.e. to at least one) of the grammatical object of the article. By way of example, "an element" means one element or more than one element. "Plurality" means at least two.

"Subject" as used herein, refers to any animal. The animal may be a mammal. Examples of suitable mammals include, but are not limited to, human and non-human primates, dogs, cats, sheep, cows, pigs, horses, mice, rats, rabbits, and guinea pigs.

"ICG" is indocyanine green, a biocompatible near-infrared fluorescent dye approved for human use.

"PBS" is phosphate buffered saline

"HSV-2" is herpes simplex type 2 virus

"HSV-2 ICP10ΔRR'" is a mutant virus in which the RR domain is deleted or inactivated in the wild-type HSV-2 virus.

The term "pfu" is plaque forming unit, the minimum number of viruses required to form one plaque (one infected area) in a cell or bacteria culture system suitable for this test.

"S.C." is spinal cord.

The following Examples are provided for purposes of illustration only, and are not intended to be limiting unless otherwise specified. Thus, the invention should in no way be construed as being limited to the following examples, but rather, should be construed to encompass any and all variations that become evident as a result of the teaching provided herein.

EXAMPLES

Example 1

Preparation of Virus Mutants

The HSV-2 ΔRR mutant can be prepared as described in Laing, J. et al., Intranasal administration of the growth compromised HSV-2 vector ΔRR prevents kainate induced seizures and neuronal loss in rats and mice, Mol. Ther. 2006 May; 13(5): 870-881, and in Peng et al., Virology 216:184 1996.

Example 2

Preparation of Compositions

Two stock solutions were prepared:
(1) ICG stock solution: 25 mg ICG in 0.8 ml $H_2O$
(2) HSV-2 ΔRR virus stock solution: $10^7$ pfu in 20 μl phosphate buffered saline (PBS).

20 μL of the virus stock solution was combined with 20 μL ICG stock solution and kept for 1 hr at 4° C. (ICG/PBS/HSV-2 ΔRR mixture).

Example 3

Animal Study

Example 3 is a comparison of imaging with a fluorescent dye alone versus a fluorescent dye bound to the virus. Unless otherwise specified, all images are digital images obtained from a CCD camera.

A mouse (60 g) was briefly anesthetized by halothane inhalation. The right footpad of the mouse was injected with 10 µL of ICG, phosphate buffered saline (PBS) and a virus mutant, HSV-2 ΔRR ("ICG/PBS/HSV-2 ΔRR mixture"). The left footpad was injected with 10 µl of ICG/PBS mixture as a control. The same concentration of ICG was present in both mixtures.

2 hours after footpad injections, the mouse was anesthetized and then euthanized with interperitoneal injection of sodium pentobarbital. ICG fluorescence images were acquired first of the intact mouse and then at various stages of dissection.

Results

Figure 3A:
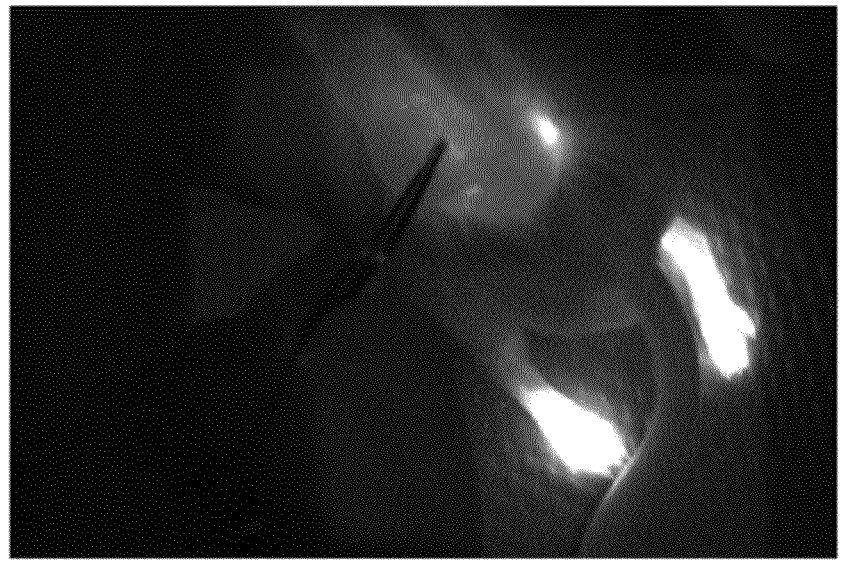
FIG. 3A shows a fluorescence image of the back of the mouse of Example 3.
Figure 3B:
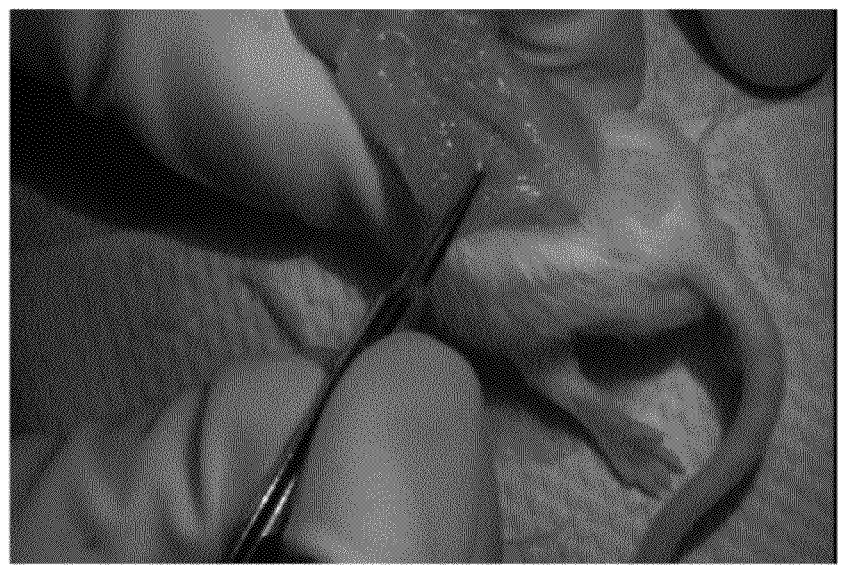
FIG. 3B is a visible (white) light image of the same back of the mouse of FIG. 3A but without fluorescence imaging.

FIG. 3A is a fluorescence image of the back of the mouse of Example 3 with the spine and back muscles exposed. The left foot fluorescence, with ICG alone injected, is limited to the left foot itself. The right foot, injected with the ICG/PBS/HSV-2 ΔRR mixture, is itself fluorescent but the fluorescence extends up to the spine where the dorsal root ganglia (i.e., the neuron cell bodies) of the foot nerves are located. The ICG-PBS-HSV-2 ΔRR complex has traveled up the axons from the foot to the axons' cell bodies at the spine. The footpad injection of ICG-PBS-HSV-2 ΔRR has traced the footpad nerves all the way to the spine. FIG. 3B depicts the same view as FIG. 3A but as a visible (white) light image without fluorescence imaging.

Figure 3C:
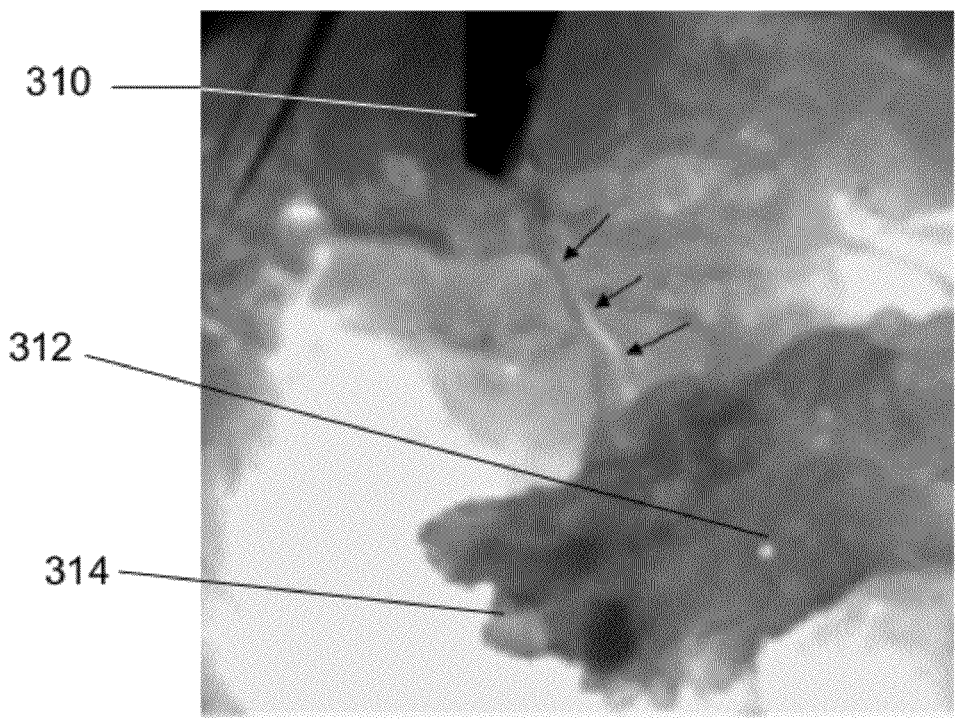
FIG. 3C is a fluorescence image with some visible light illumination of the exposed spinal cord of the mouse of Example 3.
Figure 3D:
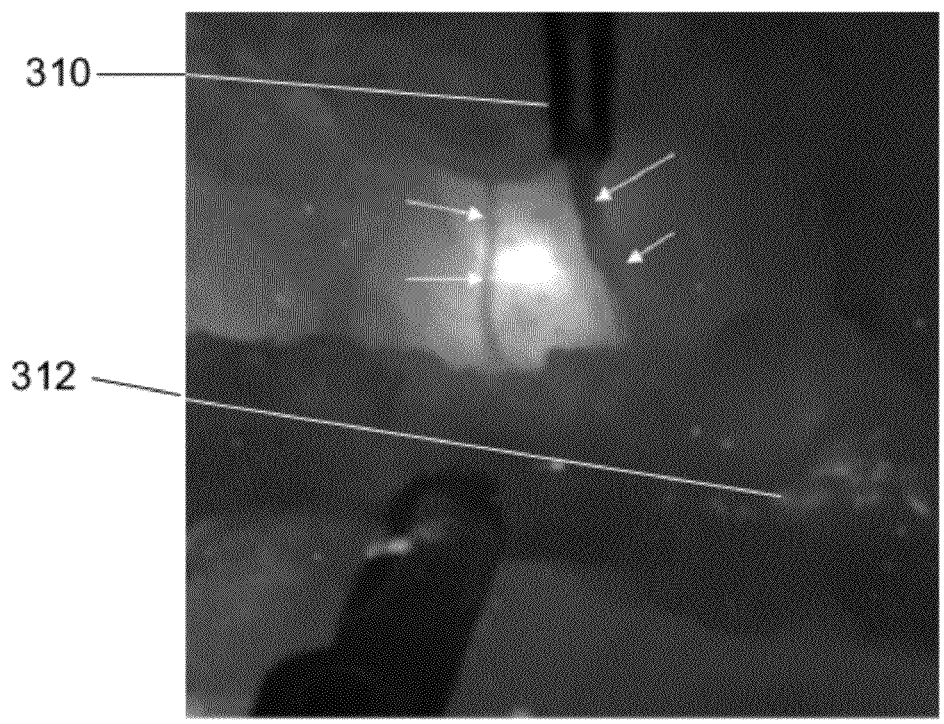
FIG. 3D is a fluorescence image of the same spinal cord closer to the head of the mouse with nerves meeting the spinal cord not labeled with ICG/PBS/HSV-2 ΔRR.

FIG. 3C is a fluorescence image (along with some visible white light illumination) of the exposed spinal cord of the mouse of Example 3. The portion of the fluorescent nerve (resulting from injection into the footpad) near where it meets the spinal cord is indicated by the three arrows. FIG. 3D is a fluorescence image of the same spinal cord closer to the head of the mouse with nerves meeting the spinal cord not labeled with ICG/PBS/HSV-2 ΔRR. FIG. 3D shows that only the footpad nerves whose axons took up and transported the fluorescent virus are labeled, as shown by the arrows, and not other, unrelated nerves. In FIGS. 3C and 3D, label 310 indicates the position of the forceps pulling the nerve away from the spinal cord, indicated at 312. The spinal cord is cut at position 314 (FIG. 3C only). The mouse head lies generally towards the right hand side of FIG. 3C whereas the mouse tail points generally towards the left hand side of the figure.

Example 4

Animal Study

Example 4 is a comparison of a fluorescent dye bound to a virus versus no injection to show that fluorescence is confined to the nerves from the left foot that connect to the left side of the spine.

A mouse (50 g) was briefly anesthetized by halothane inhalation. The mouse was injected with 10 µl of ICG/PBS/HSV-2 ΔRR mixture into left footpad, and injected with nothing into right footpad as control.

2 hours after footpad injection, the mouse was anesthetized with intraperitoneal injection of sodium pentobarbital. Subsequently, the heart was exposed, a jugular vein cut, and 10 ml of isotonic saline was injected slowly into an aerial chamber of the heart to exanguate and kill the mouse. The purpose of the exanguation was to reduce background tissue fluorescence resulting from ICG molecules in the footpad injected bolus that were not bound to the virus and which entered the lymphatic system. As with the first mouse, ICG fluorescence images were acquired first of the intact mouse and then at various stages of dissection.

Results

Figure 4A:
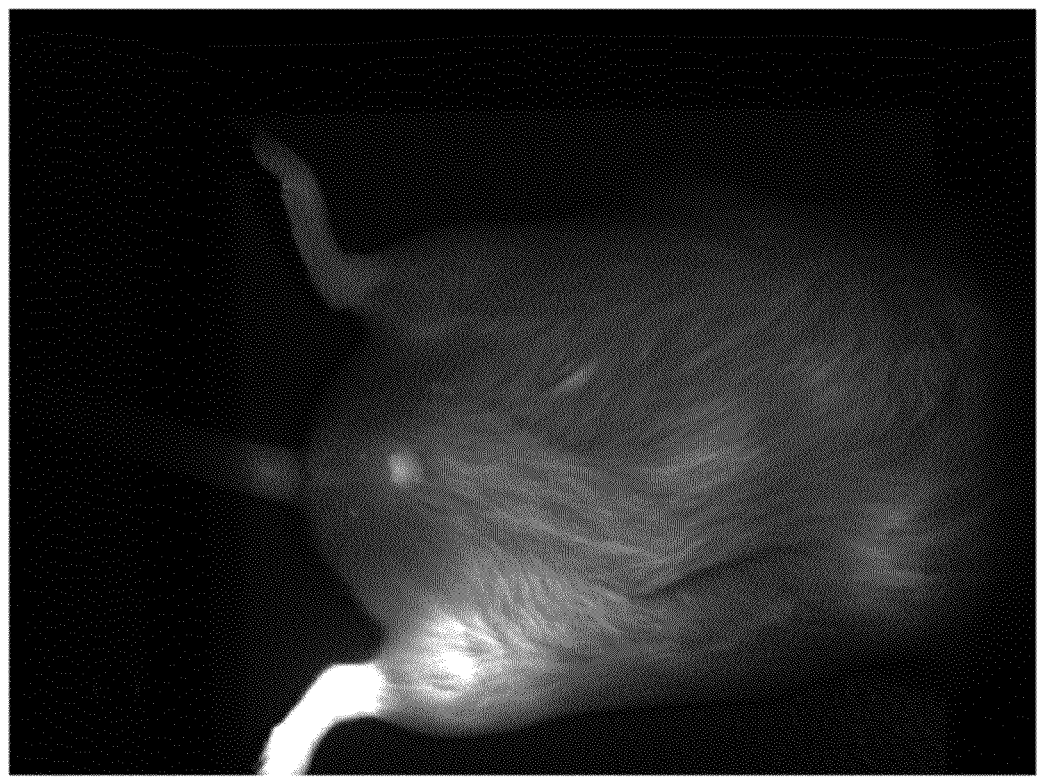
FIG. 4A shows the ICG/PBS/HSV-2 ΔRR (a dye/viral component complex) fluorescence in a ventral view of the whole mouse (lying on its back) of Example 4.

FIG. 4A shows an image of the ICG/PBS/HSV-2 ΔRR fluorescence in a ventral view of the whole mouse (the mouse is lying on its back). The left footpad injection results in fluorescence in the entire left foot and up into the left leg. The uninjected right footpad, right foot and leg are not fluorescent.

Figure 4B:
FIG. 4B is an image showing the back (dorsal view) of the mouse of Example 4 dissected to show the spine and the fluorescent nerve from the left foot, using fluorescent and white light imaging.
Figure 4C:
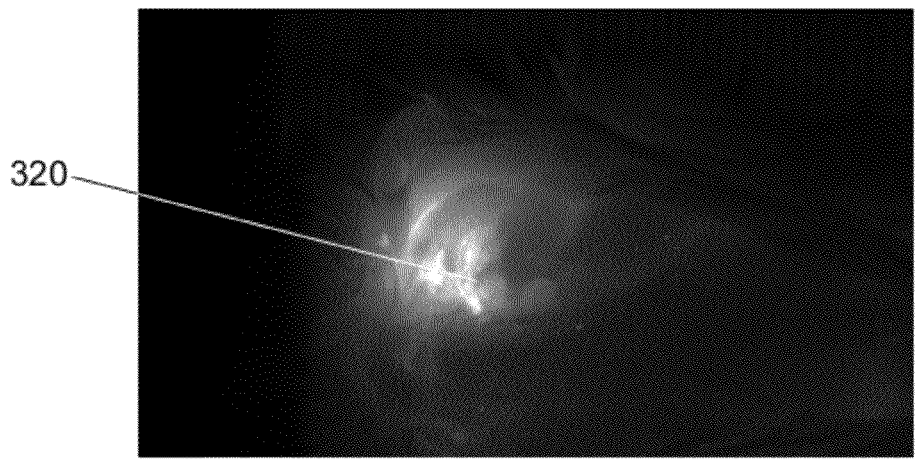
FIG. 4C is a fluorescence image of the same mouse of FIG. 4B.

FIG. 4B shows the back (dorsal view) of the mouse dissected to show the spine and the fluorescent nerve from the left foot, using fluorescent and white light imaging. Label 320 indicates the position of the nerve from the left foot. The spinal cord position is indicated at 322. FIG. 4C shows the fluorescence image alone of the same mouse. The fluorescence is confined to the left side of the spine with no fluorescence on the right (uninjected footpad) side.

Figure 4F:
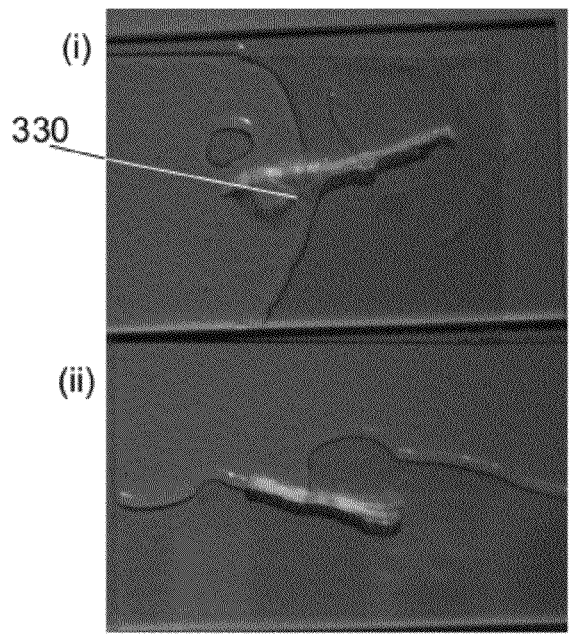
FIG. 4F is a magnified fluorescence image of the ganglion from FIG. 4E(i)
Figure 4F:
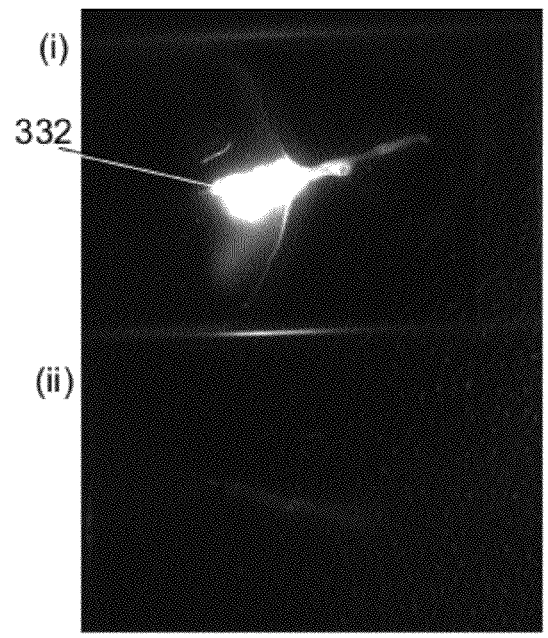
Figure 4F:
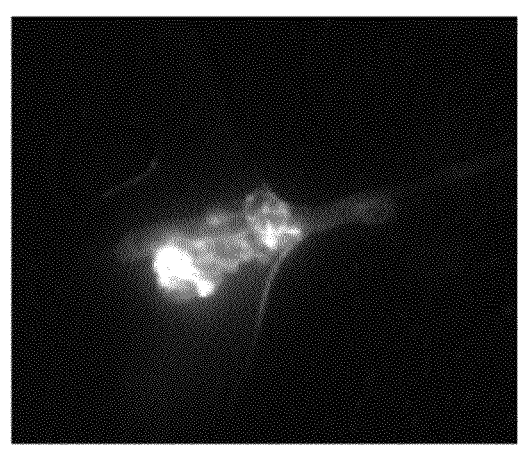

FIG. 4D shows (i) the dissected fluorescent dorsal root ganglion 330 from the left side of the spine of the mouse in white light only, with a short segment of its axons on the right side of the ganglion, and (ii) the corresponding ganglion 332 from the right side of the spine; the right foot was not injected. FIG. 4E shows (i) the fluorescence image of the ganglion of FIG. 4D(i), and (ii) the fluorescence image of the ganglion of FIG. 4D(ii). FIG. 4F shows a magnified, lower irradiance image of the ganglion from FIG. 4E(i). FIGS. 4D-4F show that injection of the left foot pad labels the left foot nerve all the way to its dorsal root ganglion and that there is no fluorescence in the corresponding right dorsal root ganglion because the right foot pad was not injected.

Example 5

UV Inactivated Virus

This Example demonstrates the imaging application of a virus inactivated by UV irradiation, rendering it replication-defective.

An ICG stock solution was prepared by dissolving 25 mg ICG in 0.8 ml $H_2O$. A virus stock solution was prepared with $10^7$ pfu of HSV-2 ΔRR in 20 µl PBS.

50 µL of the virus stock solution was combined with 50 µl ICG stock solution into one flask and was allowed to sit for 1 hr at 4° C. ("ICG/PBS/HSV-2 ΔRR mixture"). The ICG/PBS/HSV-2 ΔRR mixture above was inactivated with UV radiation at about 350 nm for about 15 minutes.

A Dutch-belted rabbit (2.57 kg) was briefly anesthetized by halothane inhalation. The rabbit was injected with 100 µl of ICG/PBS/HSV-2 ΔRR mixture into the medial toe pad of the right foot, and injected with 100 µl of UV-inactivated ICG/PBS/HSV-2 ΔRR mixture into medial toe pad of the left foot. Four and a ½ hours after performing the foot pad injections, the rabbit was anesthetized and then euthanized with an intraperitoneal injection of sodium pentobarbital. Dissection was first performed on the right limb, starting about 5 cm above the toe pad ICG/PBS/HSV-2 ΔRR injection site.

Figure 5B:
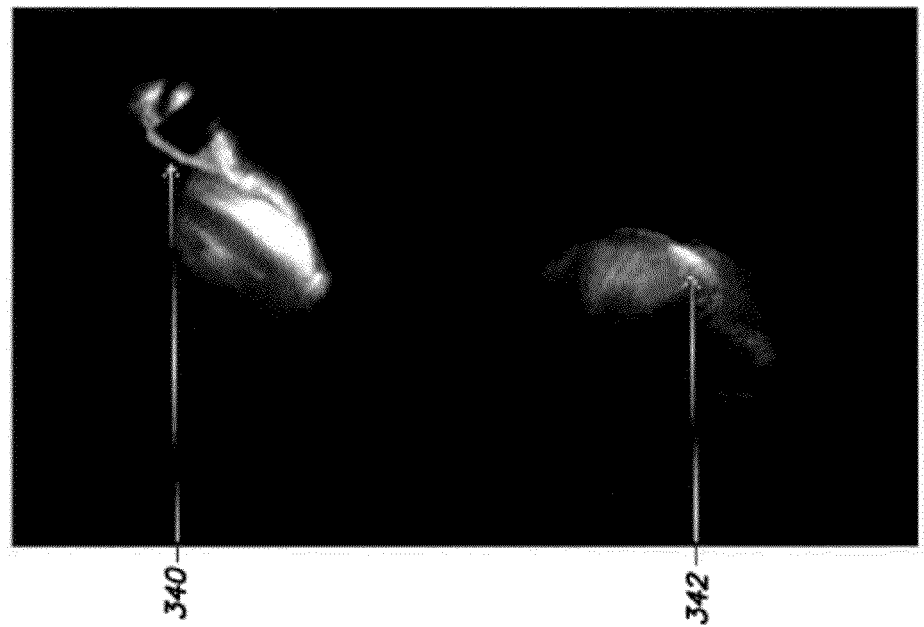
FIG. 5B is a fluorescence image showing that the ICG/HSV-2ΔRR complex traveled from the toe pad injection site up into the upper plantar nerve.
Figure 5A:
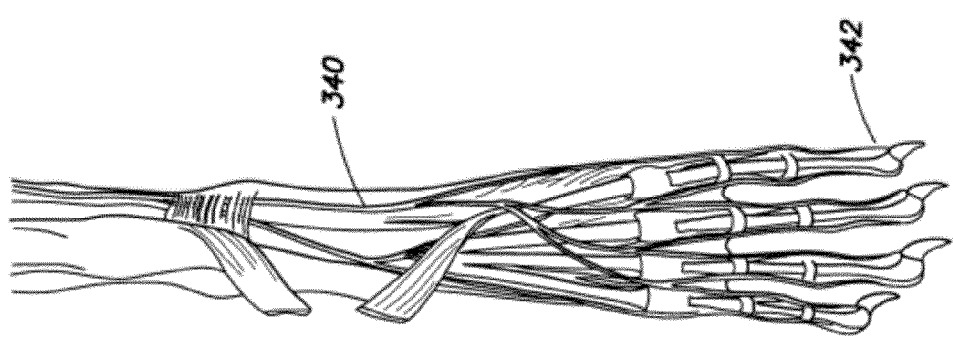
FIG. 5A shows an anatomical drawing of a rabbit left limb for comparison with the fluorescence image.

FIG. 5A is an anatomical drawing of a rabbit limb for comparison with the fluorescence image (FIG. 5B), and is presented to illustrate the position of ICG fluorescence in the right leg medial plantar nerve elevated by dissection scissors at position 340. Fluorescence from nearby blood vessels is also visible. Fluorescence at the toe pad injection site 342 is visible in the lower part of FIG. 5B.

FIG. 5C is an anatomical drawing of a medial surface of the right limb of a rabbit. The arrow indicates a large nerve adjacent to blood vessels. The same dissection procedure was carried out on the left limb into which the UV-inactivated HSV-2-ΔRR virus had been injected. Images of an isolated segment of the saphenous nerve are shown in visible light (FIG. 5D) and with ICG fluorescence (FIG. 5E), with the white arrow indicating the position of the nerve.

Figure 5F:
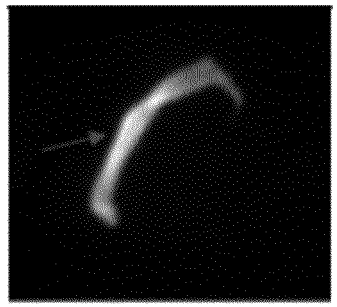
FIGS. 5F and 5H are fluorescence images showing, respectively, an excised segment of the saphenous nerve of the previous two frames (FIG. 5F) and the nerve in situ (FIG. 5H)
Figure 5G:
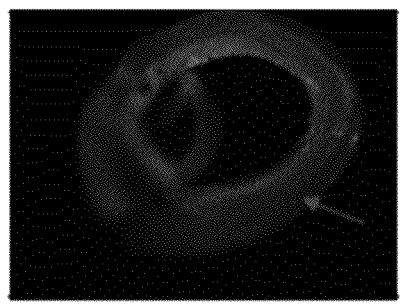
FIGS. 5G and 5I are fluorescence images showing the excised segment of the saphenous nerve of FIG. 5F but stained for the LacZ gene of the UV-inactivated ICG/PBS/HSV-2 ΔRR virus.
Figure 5H:
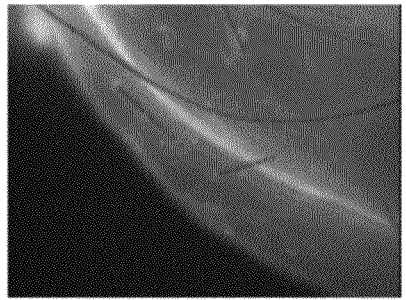
Figure 5I:
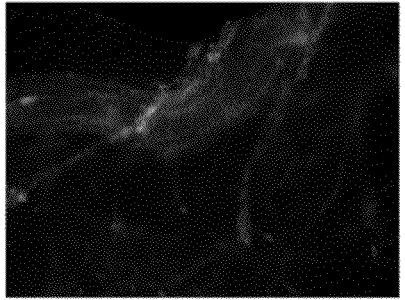

The isolated nerve segment was excised and placed on a microscope slide. After moistening it with isotonic saline, a cover slip was applied. ICG fluorescence of the segment can be seen in FIG. 5F as recorded by the SPY system (sold by Novadaq Technologies Inc., Mississauga, Canada). The nerve ICG fluorescence also had been recorded in situ at 10× magnification (FIG. 5H). The nerve segment was then stained with an enzyme (C12-FDG) that stains LacZ (the gene that replaced the gene segment sliced from the HSV-2 virus to attenuate it). Micrographs of the stained nerve are shown at two magnifications (FIG. 5G, 4× magnification and FIG. 5I, 10× magnification), indicating presence of the virus in the nerve.

Figure 5K:
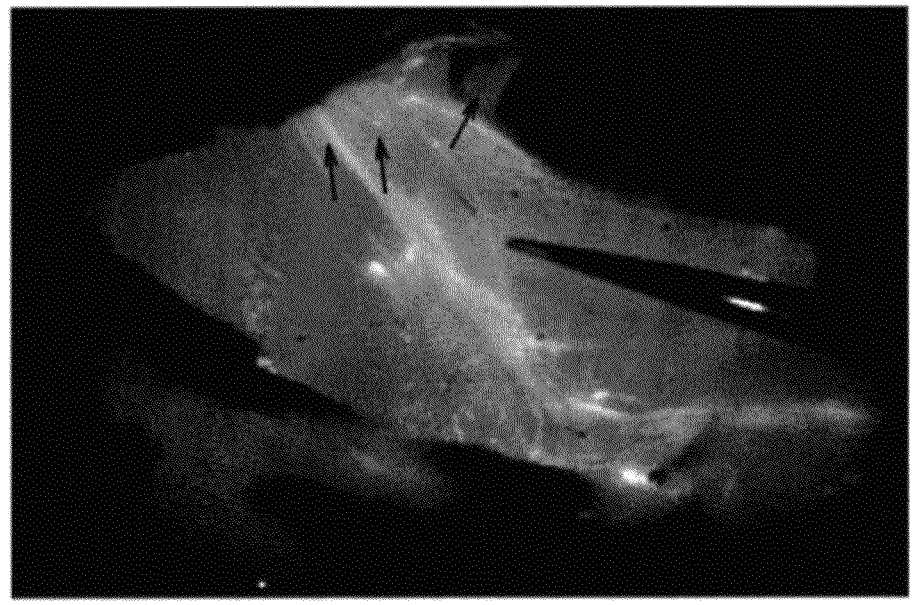
FIG. 5K is a fluorescence image of the dorsal aspect of the left leg of the rabbit of Example 5.
Figure 5J:
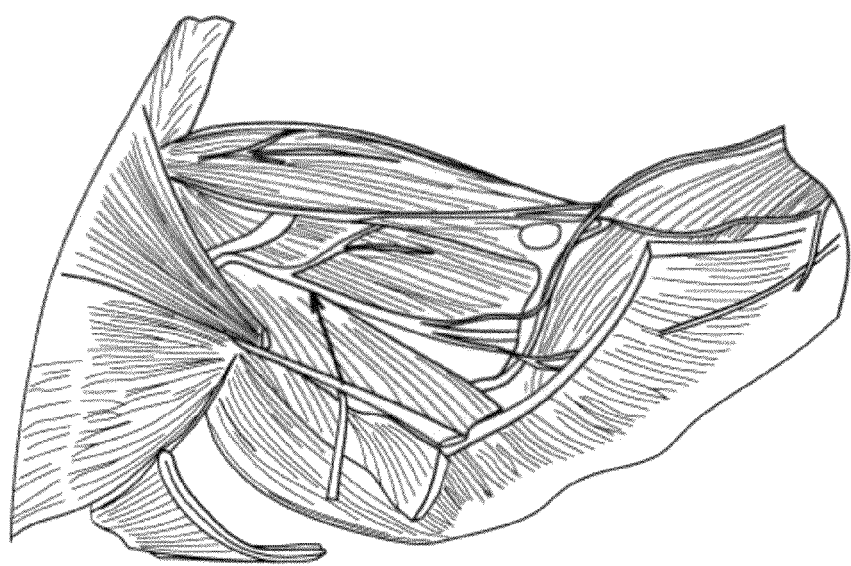
FIG. 5J is an anatomical drawing of the rabbit left limb for comparison with the fluorescence image.

FIG. 5K shows a fluorescence image of the dorsal aspect of the left leg of the rabbit of Example 5, an anatomical drawing of which is shown in FIG. 5J. The arrow in FIG. 5J points to a large nerve in the upper limb. FIG. 5K demonstrates that the ICG/PBS/HSV-2 ΔRR traveled from the toe pad injection site up into the upper plantar nerve. The ICG UV-inactivated virus moved into small branches of what are presumed to be the ischiadic and tibial nerves (arrows), which allowed imaging of even these small nerves. The arrows are about 11 cm above the toe pad injection site, indicating that the fluorescent UV-inactivated virus traveled 11 cm above the toe pad, allowing even distant nerves to be imaged. FIG. 5K right also likely shows fluorescence in blood vessels.

Many modifications and variations can be made as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

The invention claimed is:

1. A composition comprising:
   a fluorescent dye; and
   a neurotropic herpes varicellae unable to replicate in nerve cells,
   wherein the fluorescent dye is bound to the virus to form a complex that is capable of penetrating nerve cells.

2. The composition of claim 1, wherein the dye is selected from indocyanine green, infracyanine green, green fluorescent dye, fluorescein isothiocyanate, rhodamine, phycoerythrin, phycocyanin, allophycocyanin, o-phthaldehyde, fluorescamine, Rose Bengal, trypan blue, fluoro-gold, 3-indocyanine-green-acyl-1,3-thiazolidine-thione, green fluorescent protein, red fluorescent protein, yellow fluorescent protein, blue fluorescent protein and other fluorescent proteins.

3. The composition of claim 2, wherein the dye is indocyanine green.

* * * * *